United States Patent [19]

Bruno

[11] Patent Number: 4,481,212

[45] Date of Patent: Nov. 6, 1984

[54] THIOLACTIC ACID DERIVATIVE WITH BRONCHOSECRETOGOGUE ACTIVITY

[75] Inventor: Graziella Bruno, Milan, Italy

[73] Assignee: Medea Research s.r.l., Milan, Italy

[21] Appl. No.: 588,953

[22] Filed: Mar. 13, 1984

[30] Foreign Application Priority Data

Mar. 23, 1983 [IT] Italy .............................. 20236 A/83

[51] Int. Cl.³ ..................... A61K 31/38; C07D 333/00
[52] U.S. Cl. ....................................... 424/275; 549/59
[58] Field of Search ........................... 549/59; 424/275

[56] References Cited

U.S. PATENT DOCUMENTS 4,344,956  8/1982  Ercoli .................................. 549/59

Primary Examiner—Alan Siegel
Attorney, Agent, or Firm—Bucknam and Archer

[57] ABSTRACT

The 2-(2-thenoylthio)-N-(2',3',4',5',-tetrahydro-2'-oxo-thiophen-3'-yl)-propionylamide having formula I

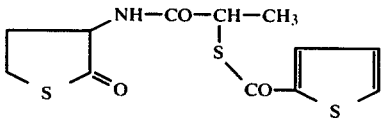

is endowed with marked bronchosecretogogue activity.

3 Claims, No Drawings

THIOLACTIC ACID DERIVATIVE WITH BRONCHOSECRETOGOGUE ACTIVITY

The invention refers to 2-(2-thenoylthio)-N-(2',3',4',5'-tetrahydro-2'-oxo-thiophen-3'-yl)-propionylamide having formula I

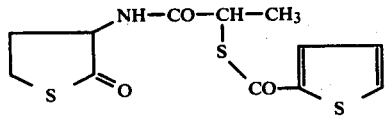

The compound I, hereinafter defined also, for brevity, with the abbreviation MR-889, is endowed with interesting pharmacological properties which make it useful for the treatment of the respiratory system diseases, both of acute and chronic nature, such as for instance bronchitis, bronchopolmonitis, rhynitis, otitis and generally for the respiratory and O.R.L. apparatus diseases characterized by increased consistence and amount of mucuspurulent secretions.

MR 889 is in fact endowed with potent bronchosecretogogue action, as it was shown in the experimental animal by evaluating the sodium fluorescein bronchial elimination.

The compound according to the invention can be conveniently prepared by reacting homocysteine thiolactone hydrochloride with a reactive derivative of S-thenoyl-thiolactic acid, in the presence of anhydrous aprotic solvents and of acidity acceptors.

Preferably the reactive derivative is obtained by reaction of S-thenoyl-thiolactic acid with ethyl chlorocarbonate, at temperatures ranging from $-10°$ to $+10°$ C. As acidity acceptors, tertiary amines such as triethylamine, are preferably used.

The following example illustrate, in non limitative way, the preparation method of the compound according to the invention.

EXAMPLE 7.25 G of triethylamine are added to 15.5 g of S-thenoyl-thiolactic acid in 100 ml of anhydrous tetrahydrofuran.

The mixture is cooled to $-5°$ C. under stirring, and 7.8 g of ethyl chlorocarbonate are added thereto keeping the temperature from $0°$ to $10°$ C. A solution of 11 g of homocysteine thiolactone hydrochloride and 10 ml of triethylamine in 30 ml of water is added to the reaction, keeping the temperature below $10°$ C. The reaction is then left, always under stirring, for 1 hour at room temperature.

At the end the solvent is evaporated under reduced pressure, and the residue is washed with water and extracted with diethyl ether. The organic phase is dried on anhydrous sodium sulphate and the solvent is distilled off under reduced pressure.

The crude product obtained is crystallized from a 60:40 dichloromethane/diethyl ether mixture. The crystallized product melts at $115°$-$120°$ C. 7.5 g were obtained.

The reaction course has been checked by means of T.L.C. Eluents: diethyl ether/methanol 10:1.

The following analysis have been carried out on the so obtained product:

I.R. (recorded in nujol mull, the values of the absorption bands are given in cm$^{-1}$):

| | |
|---|---|
| stretch N—H | 3270 |
| stretch C=O thioester | }  |
| stretch C=H thiolactone | 1695 strong |
| stretch C=O amide | 1645 strong |

H$^1$ N.M.R. (recorded in CDCl$_3$+DMSO 5% using TMS as internal standard. The proton chemical shifts values are in δ).

| | |
|---|---|
| 1.6 | (d, 3H, —CH$_3$); |
| 1.9-2.9 | (m, 2H, CH$_2$—CH—NH); |
| 3.1-3.7 | (m, 2H, —CH$_2$S); |
| 4.1-4.8 | (m, 2H, —CH—CH$_3$, —CH—NH); |
| 7-7.8 | (m, 3H aromatics, 1 NH mobile). |

The biological characteristics of MR 899 are hereinafter described.

Bronchosecretogogue activity

The bronchosecretogogue activity of MR 899 and of an experimented drug having known activity, S-carboxymethylcysteine, has been valued in the rat by using the method described by Mawatari ("Experimental Studies on the Expectorant Action of Several Drugs", Kagoshima Daigaku Igaku Zasshi., 27, 561, 1976).

The compounds under examination have been administered by the oral route at equiponderal doses 30 minutes after the subcutaneous administration of sodium fluorescein.

Thereafter, following the animals' sacrifice, the evaluation of the sodium fluorescein amount present at the bronchial level has been carried out.

The obtained results, reported in Table I, are expressed as percent increase of the bronchial elimination of sodium fluorescein of the MR 889 and S-carboxymethylcysteine treated groups in comparison with a control group.

MR 889 has shown a very good bronchosecretogogue activity, nearly equal to that of S-carboxymethylcysteine, with a 70.9% increase, significant ($p<0.05$) in the used experimental conditions.

TABLE I

| | BRONCHOSECRETOGOGUE ACTIVITY | | | | |
|---|---|---|---|---|---|
| | | | | FLUORESCEIN | |
| TREATMENT | DOSE mg/kg i. p. | No animals | Animals weight grams | Sodium μg/ml | % versus controls |
| CONTROL | — | 5 | 99.0 ± 5.56 | 0.31 ± 0.02 | — |
| S—CARBOXY-METHYL-CYSTEINE | 500 | 5 | 95.0 ± 7.41 | 0.54* ± 0.05 | 74.2 |
| MR 889 | 500 | 5 | 101.0 ± 2.91 | 0.53* ± 0.06 | 70.9 |

Student test* $p < 0.05$

The present invention refer also to all the industrially applicable aspects connected with the use of MR 889 as mucoregulating and bronchosecretogogue agent. An essential aspect of the invention is therefore provided by pharmaceutical compositions containing predetermined and therapeutically effective amounts of MR 889, suitable for the oral, rectal, parenteral or inhalatory administrations.

Non limitative examples of such pharmaceutical compositions are therefore provided by capsules, tablets, pills, syrups, suppositories, vials of bottles for injection, aerosols, possible sustained release forms, obtained for instance by microincapsulation, containing from 50 to 1000 mg of MR 889 in addition to the excipients commonly used in pharmaceutical technique.

I claim:

1. 2-(2-Thenoylthio)-N-(2',3',4',5'-tetrahydro-2'-oxo-thiophen-3'-yl)-propionylamide having formula I

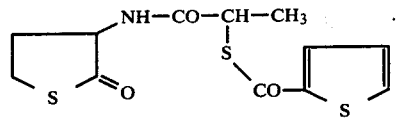

2. Pharmaceutical compositions with mucusregulating and bronchosecretogogue activity characterized by containing as active principle therapeutically active amounts of the compound according to claim 1.

3. Pharmaceutical compositions according to claim 2 in form of capsules, pills, tablets, syrups, suppositories, solutions.

* * * * *